US007491696B2

(12) United States Patent
Eming et al.

(10) Patent No.: US 7,491,696 B2
(45) Date of Patent: Feb. 17, 2009

(54) PROTEOLYSIS RESISTANT ACTIVE VEGF

(75) Inventors: Sabine Eming, Cologne (DE); Thomas Krieg, Cologne (DE); Stephan Sollberg, Schwerin (DE); Gereon Lauer, Radolfzell (DE)

(73) Assignee: Bayer Innovation GmbH (DE)

( * ) Notice: Subject to any disclaimer, the term of this patent is extended or adjusted under 35 U.S.C. 154(b) by 0 days.

(21) Appl. No.: 10/506,893

(22) PCT Filed: Mar. 6, 2003

(86) PCT No.: PCT/EP03/02289

§ 371 (c)(1),
(2), (4) Date: Sep. 1, 2005

(87) PCT Pub. No.: WO03/076625

PCT Pub. Date: Sep. 18, 2003

(65) Prior Publication Data

US 2006/0148687 A1    Jul. 6, 2006

(30) Foreign Application Priority Data

Mar. 8, 2002    (EP)    .................................. 02005186

(51) Int. Cl.
*A61K 38/18*    (2006.01)
*C07K 14/475*    (2006.01)
*C12N 15/18*    (2006.01)
*C12N 15/63*    (2006.01)

(52) U.S. Cl. .............................. 514/12; 514/2; 530/399; 435/69.1; 435/320.1; 536/23.5

(58) Field of Classification Search ........................ None
See application file for complete search history.

(56) References Cited

U.S. PATENT DOCUMENTS 5,219,739 A * 6/1993 Tischer et al. .............. 435/69.4
6,057,428 A * 5/2000 Keyt et al. .................. 530/399

OTHER PUBLICATIONS

Powers, J.C. et al, "Proteases-structures, mechanism and inhibitors", NCBI abstract of Agents Actions Suppl., 42: 3-18 (1993) (Abstract).
Robinson, C. J. et al, "The splice variants of vascular endothelial growth factor (VEGF) and their receptors", Journal of cell Science, England, Vo. 114, No. Pt 5 (Mar. 2001).
Scharffetter-Kochanek, K. et al, "Chronische Wunden und Wachstumsfaktoren Chronic wounds and growth factors", Zeitschrift für Hautkankheiten, H&G, 11 (74): 664-672 (1999).
Soker, S. et al, "Neuropilin-1 Is Expressed by Endothelial and Tumor Cells as an Isoform-Specific Receptor for Vascular Endothelial Growth Factor", Cell, vol. 92: 735-745 (Mar. 20, 1998).
Wu, X.C. et al, "Engineering of plasmin-resistant forms of streptokinase and their production in Bacillus subtilis: streptokinase with longer functional half-life", Appl Environ Microbiol., 64(3):824-9 (Mar. 1998).
Powers, J.C. et al, "Proteases-structures, mechanism and inhibitors", in *Proteases, Protease Inhibitors and Protease Derived Peptides*, Agents Actions Suppl., 42: 3-18 (Publ. Birkhaeuser, 1993).
Frank, S. et al, "Regulation of Vascular Endothelial Growth Factor Expression in Cultured Keratinocytes Implications for Normal and Impaired Wound Healing", JBC Online, vol. 270, No. 21: 12607-12613 (May 16, 1995).
Fukumura, D. et al, "Tumor Induction of VEGF Promoter Activity in Stromal Cells", Cell, vol. 94: 715-725 (Sep. 18, 1998).
Gospodarowicz, D. et al, "Isolation and characterization of a vascular endothelial cell mitogen produced by pituitary-derived folliculo stellate cells", Proc. Natl. Acad. Sci. USA, vol. 86: 7311-7315 (Oct. 1989).
Keck, P. et al, "Vascular Permeability Factor, an Endothelial Cell Mitogen Related to PDGF", Science, vol. 246: 1309-1312 (Dec. 8, 1989).
Keyt, B. et al, "The Carboxyl-terminal Domain (111-165) of Vascular Endothelial Growth Factor Is Critical for Its Mitogenic Potency", The Journal of Biological Chemistry, vol. 271, No. 13: 7788-7795 (Mar. 29, 1996).
Lauer, G. et al, "Expression and Proteolysis of Vascular Endothelial Growth Factor is Increased in Chronic Wounds", The Journal of Investigative Dermatology, vol. 115, No. 1: 12-18 (Jul. 2000).
Lauer, G. et al, "Expression of the soluble variant of the vascular endothelial growth factor receptor Flt-1 in chronic wounds", Wound Repair and Regeneration, Vo. 8, No. 5 (Sep. 2000).
Lauer, G. et al, "Generation of a novel proteolysis resistant vascular endothelial growth factor 165 variant by a site-directed mutation at the plasmin sensitive cleavage site", FEBS Lett., 531(2):309-13 (Nov. 6, 2002).
Lauer, G. et al, "VEGF Expression chronic non-healing wounds", Archives of Dermatological Research, vol. 293, No. 1-2, P145, p. 79 (Feb. 2001).
Lawrence, W. et al, "*Growth Factors in Wound Healing*", Clinics in Dermatology, 12: 157-169 (1994).
Market, Y. et al, "Increased proteolytic resistance of ribonuclease A by protein engineering", Protein Engineering, England, vol. 14, No. 10 (Oct. 2001).
Mohanraj, D. et al, "Expression of Biologically Active Human Vascular Endothelial Growth Factor in Yeast", Growth Factors, vol. 12: 17-27 (1995).
Nissen, N. et al, "Vascular Endothelial Growth Factor Mediates Angiogenic Activity during the Proliferative Phase of Wound Healing", American Journal of Pathology, vol. 152, No. 6: 1445-1452 (Jun. 1998).

* cited by examiner

*Primary Examiner*—Christine J Saoud
(74) *Attorney, Agent, or Firm*—Joyce von Natzmer; Pequignot + Myers LLC

(57) ABSTRACT

The invention relates to endothelial growth factor (VEGF) in which the alanine at AA position 111 is replaced by proline. The arginine at AA position 110 may moreover be replaced by another amino acid. The invention also relates to derivatives of the VEGF according to the invention, nucleic acids, expression systems, medicaments and the use of the VEGF mutants of the invention for the treatment of chronic wounds.

19 Claims, 5 Drawing Sheets

PROTEOLYSIS RESISTANT ACTIVE VEGF

Figure 1:
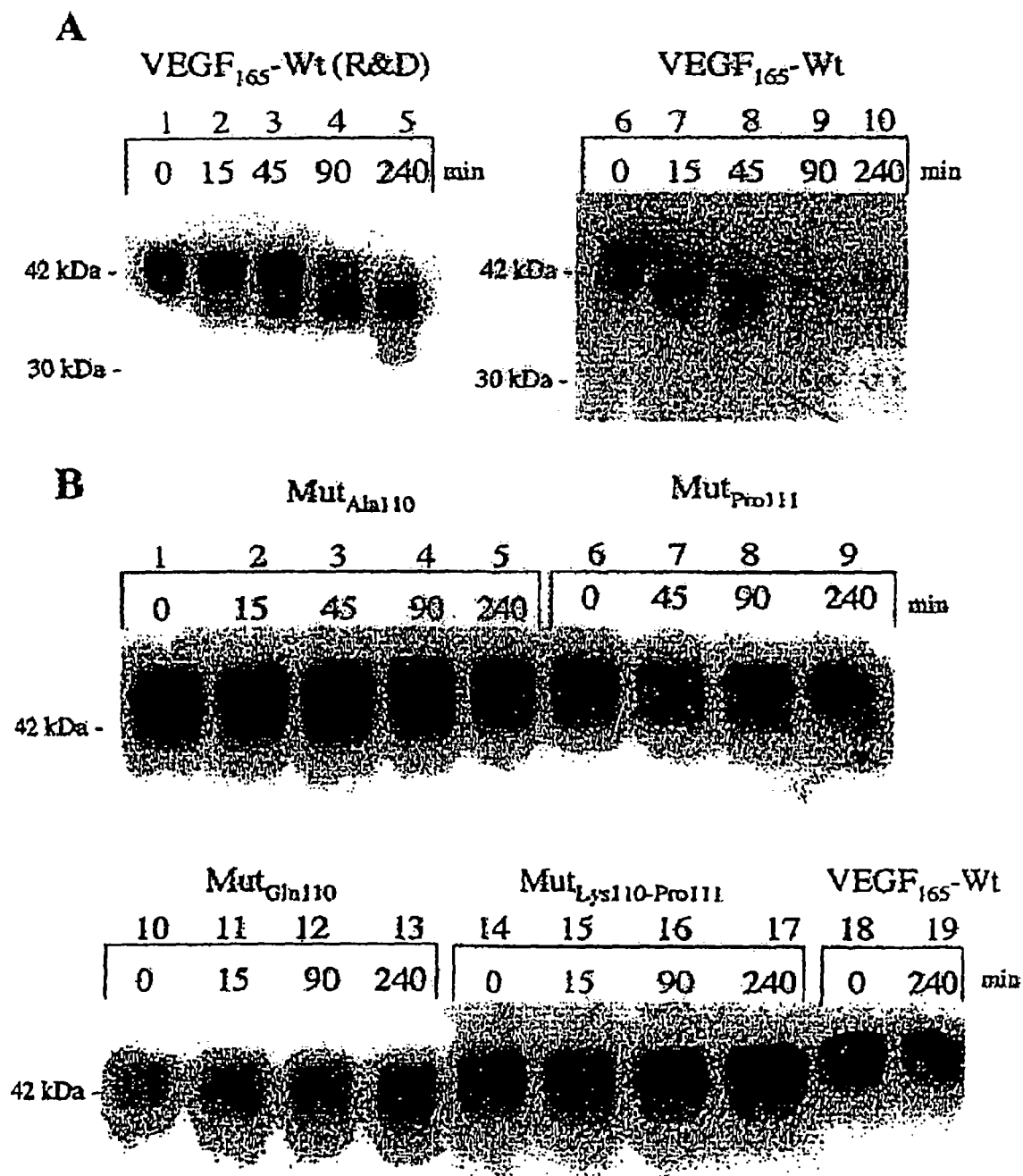

This is the U.S. national stage of International application PCT/EP2003/02289, filed Mar. 6, 2003 designating the United States and claiming priority to European application 02005186.8, filed Mar. 8, 2002.

FIELD OF THE INVENTION

The invention relates to vascular endothelial growth factor (VEGF) in which the alanine at AA position 111 is replaced by proline. The arginine at AA position 110 may moreover be replaced by another amino acid. The invention also relates to derivatives of the VEGF according to the invention, nucleic acids, expression systems, medicaments and the use of the VEGF mutants of the invention for the treatment of chronic wounds.

BACKGROUND OF THE INVENTION

An important stage in cutaneous wound healing is the formation of a granulation tissue. Firstly associated with the latter is the migration in of newly formed vessels (neoangiogenesis). Numerous experimental and clinical studies show that chronic wounds are characterized by impaired angiogenesis and thus diminished formation of granulation tissue.

A large number of mediators which stimulate angiogenesis during wound healing are known. They include firstly the factors which, besides stimulating endothelial cells, also activate mesenchymal and/or epidermal cells (bFGF, aFGF, TGF-a, PDGF), and secondly so-called endothelial cell-specific factors whose receptors are substantially confined to endothelial cells (VEGF, angiopoietin). A large number of physiological and pathological reactions involving the blood vessels correlates with an increased expression of VEGF and its receptors, so that VEGF assumes a central role in angiogenesis of the skin. The first indications of the possible importance of VEGF in wound healing impairments were provided on the basis of experiments on VEGF expression in diabetic mice (db/db mice) (Frank et al. 1995). It was possible to show in this model that the wound healing impairment correlates with a diminished VEGF expression. It has recently been possible to provide support for the role of VEGF in wound healing by a further transgenic animal model (Fukumura et al., 1998) and detection of VEGF in the wound discharge from acute human wounds (Nissen et al., 1998).

It has further been shown that there is increased expression of the mRNA of VEGF and its receptors in the tissue of chronic wounds (Lauer et al., 2000). Investigations by SDS-PAGE show, however, breakdown of the VEGF protein in the chronic wound environment, in contrast to the acute wound. This breakdown leads to a significant loss of the biological activity and may thus, despite the increased expression of the VEGF receptors, underlie a deficient stimulation of neoangiogenesis in the chronic wound environment. As explained above, it was possible to show that plasmin is involved in the cleavage of VEGF in the chronic wound environment (Lauer et al., 2000).

Cleavage of $VEGF_{165}$ via plasmin leads to detachment of the carboxyl-terminal domain which is encoded by Exon 7. Whereas Exons 3 and 4 determine the binding properties of VEGF to the VEGF receptors Flt-1 and Flk-1/KDR, Exon 7 has a critical importance in the interaction of VEGF with neuropilin-1 (Keyt et al. 1996). Neuropilin-1 is a 130 kDa cell surface glycoprotein. Its role in the potentiation of the mitogenic effect of VEGF on endothelial cells was described only recently (Soker et al. 1998). In this connection, the interaction of neuropilin-1 with Flk-1/KDR appears to be important because binding solely of VEGF to neuropilin-1 has no signal effect.

Plasmin belongs to the class of serine proteases. These enzymes are able to cleave peptide linkages. The cleavage takes place by a so-called catalytic triad. In the catalytic centre thereof an essential part is played in particular by the eponymous serine, but also by the amino acids histidine and aspartate, because the process of peptide cleavage takes place by means of them (Stryer 1987, pp. 231 et seq.). Although the mechanism of the linkage cleavage is identical in all serine proteases, they differ markedly in their substrate specificity. Thus, plasmin, just like trypsin, cleaves peptide linkages after the basic amino acids lysine and arginine. However, the substrate specificity of plasmin, which is determined by the structure of the catalytic centre, leads to plasmin being unable to cleave all these linkages. Catalysis of peptide-linkage cleavage is possible only if the corresponding protein segments are able to interact with the catalytic centre of the enzyme (Powers et al. 1993; Stryer 1987). To date, no unambiguous consensus sequence of a plasmin cleavage site is known.

The present invention is based on the object of providing improved means for healing chronic wounds. Surprisingly, this object is achieved by the provision according to the invention of a vascular endothelial growth factor (VEGF) variant which is characterized in that at least one amino acid in the sequence of the native vascular endothelial growth factor at positions 109 to 112 of the native vascular endothelial growth factor is replaced by another amino acid or a deletion.

BRIEF SUMMARY OF THE INVENTION

In one embodiment of the invention, at least one amino acid in the sequence of the native vascular endothelial growth factor is replaced by proline in the VEGF variant according to the invention the positions 109 to 112. In a further embodiment, besides proline, at least one further amino acid at one of positions 109 to 112 in the VEGF according to the invention is replaced or a deletion.

In a further embodiment, the alanine at AA position 111 of the native vascular endothelial growth factor is replaced by proline in the VEGF variant according to the invention.

In another embodiment, the arginine at AA position 110 of the native vascular endothelial growth factor is replaced by another amino acid in the VEGF variant according to the invention. In particular, the arginine at AA position 110 of the native vascular endothelial growth factor is replaced by proline.

In a further embodiment of the invention, the alanine at AA position 111 of the native vascular endothelial growth factor is replaced by another amino acid in the VEGF.

It is possible in particular for the arginine at AA position 110 of the native vascular endothelial growth factor and the alanine at AA position 111 of the native vascular endothelial growth factor to be replaced by proline in the VEGF variant according to the invention.

The VEGF mutants according to the invention are preferably in the form of one of the splice variants $VEGF_{121}$, $VEGF_{145}$, $VEGF_{165}$, $VEGF_{183}$, $VEGF_{189}$ or $VEGF_{206}$.

The VEGF mutants according to the invention display not only markedly increased stability towards plasmin, but also an activity comparable to that of wild-type VEGF. Surprisingly, the VEGF variants according to the invention additionally display distinctly increased stability in chronic wound fluids.

The mutations have been carried out at a site which is critical for the biological activity of the VEGF molecule. There was thus a fear that a change in the protein structure in this region has a negative effect on the activity of $VEGF_{165}$. The amino acid proline, which is introduced according to the invention at position 111, is a cyclic α-imino acid. Owing to the cyclic form of the pyrrolidine residue, it has a rigid conformation which also has an effect on the structure of the respective proteins. Thus, proline acts for example as a strong α-helix breaker. It is therefore particularly surprising that replacement precisely of alanine at position 111 by proline generates a VEGF mutant which is stable towards the protease plasmin, is stable in chronic would fluids and, at the same time, still has an activity corresponding to that of the wild-type protein.

The invention relates in particular to VEGF variants of the two sequences Seq. No. 1 or Seq. No. 2.

The invention also relates to variants of the VEGF mutants mentioned above, in which the amino acid sequences are modified or derivatized, or comprise mutations, insertions or deletions. This relates in particular to VEGF variants in which further single amino acids are replaced, and those which are glycosylated, amidated, acetylated, sulphated or phosphorylated. Such VEGF variants preferably have an activity comparable to or higher than the wild-type VEGF.

The VEGF variants according to the invention may also have a signal sequence. The signal sequence may be connected N-terminally to the amino acid chain of the VEGF variant and have the sequence

```
                                        (SEQ ID NO:3)
Met Asn Phe Leu Ser Trp Ser Val His Trp Ser Leu

Ala Leu Leu Leu Tyr Leu His His Ala Lys Trp Ser

Gln Ala.
```

The invention also relates to nucleic acids which code for the abovementioned VGEF mutants, and vectors for VEGF expression which comprise such nucleic acids.

The invention relates to a medicament which comprises the abovementioned mutants of VEGF, and to the use of the VEGF mutants for producing a medicament for the treatment of chronic wounds, caused by vascular lesions such as chronic venous insufficiency (CVI), primary/secondary lymphoedema, arterial occlusive disease, metabolic disorders such as diabetes mellitus, gout or decubitus ulcer, chronic inflammatory disorders such as pyoderma gangrenosum, vasculitis, perforating dermatoses such as diabetic necrobiosis lipoidica and granuloma annulare, haematological primary disorders such as coagulation defects, sickle cell anaemia and polycythemia vera, tumours, such as primary cutaneous tumours and ulcerative metastases, and for plasmin inhibition, for inducing neoangiogenesis and/or for inhibiting matrix degradation.

BRIEF DESCRIPTION OF THE DRAWINGS

FIG. 1, consisting of FIGS. 1A and 1B, shows that the $VEGF_{165}$ mutations are resistant to cleavage by plasmin. The figure shows incubation of $VEGF_{165}$ and the mutated proteins in a plasmin solution [0.01 U/ml] or buffer solution (FIG. 1B, lanes 18, 19) for the stated periods. Analysis of the degradation behaviour took place by Western blotting and immunodetection.

FIGS. 2A to 2C show that the $Ala_{111}$ to $Pro_{111}$ mutation increase the stability of VEGF in chronic wound fluid. FIG. 2A: $VEGF_{165}$ wild type expressed in COS-1 cells. FIG. 2B: the VEGF variants were incubated in chronic wound fluid for the stated periods, and the degradation behaviour was visualized by immunodetection. In this case, wound fluids from two different patients were investigated: patient X, lanes 1-16; patient Y: lanes 17-20). FIG. 2C: Densitometric visualization of the degradation of VEGF wild type and $Mut_{Lys\text{-}Pro}$ in chronic wound fluid. The relative signal strength from three independently performed Western blot analyses (mean +/−SD) is shown.

FIG. 3 shows that the VEGF mutants are biologically active. $VEGF_{165}$ wild type and VEGF mutants were each incubated in increasing concentrations with HUVE cells. The rate of incorporation of the base analogue into the DNA of the proliferating cells determined by BrdU ELISA is shown (mean +/−SD; n=3).

FIGS. 4A to 4D show that plasmin does not alter the biological activity of the $VEGF_{165}$ mutants. A comparison is shown of the relative BrdU incorporation into HUVE cells through stimulation with $VEGF_{165}$ wild type (FIG. 4A, FIG. 4B), $Mut_{Ala}$ (FIG. 4C) and $Mut_{Lys\text{-}Pro}$ (FIG. 4D) after incubation of the stated protein in buffer or plasmin (means +/−SD; n=3).

DESCRIPTION OF VARIOUS AND PREFERRED EMBODIMENTS OF THE INVENTION

Topical use of growth factors represents a novel therapeutic concept in wound healing. It has been possible to observe an improvement in the healing of chronic wounds in a large number of clinical studies with the use of EGF, bFGF, PDWHF and PDGF (Scharffetter-Kochanek et al. 2000). However, a criticism which should be noted is that the results of these studies did not come up to the expectations which existed in view of the good activity of these mediators in animal models (Lawrence et al. 1994). This restricted activity of the growth factors is certainly substantially explained by the increased proteolytic activity in the chronic wound environment, which leads to degradation of the topically applied factors. It is thus clear that local wound management by administration of growth factors represents a promising novel therapeutic strategy. However, it is necessary to develop strategies which control the proteolytic activity in the chronic wound environment. The production of master cytokines with increased stability in the chronic wound environment certainly represents a novel therapeutic approach in this connection. The VEGF mutants according to the invention are particularly suitable, because of their high stability in the wound fluid, for the topical treatment of chronic wounds.

EXEMPLARY EMBODIMENT

Mutagenesis:

Four mutants were produced by site-directed mutagenesis by carrying out targeted amino acid replacements at $Arg_{110}$ and $Ala_{111}$. The cDNA which codes for human $VEGF_{165}$ was cloned into the SV40 replication expression vector pcDNA 3.1 (from Invitrogen, De Schelp, NL) using the BamHI and EcoRI cleavage sites in the cloning site. The Gene Editor™ system from Promega (Mannheim) was used for the site-directed in vitro mutagenesis. This system is based on annealing of oligonucleotides which harbour the appropriate mutation onto the initial sequence. The initial sequence of $VEGF_{165}$ in the region of the mutations is:

```
                                                 (SEQ ID NO:4)
        106 107 108 109 110 111 112 113
        GA  CCA AAG AAA GAT AGA GCA AGA CAA G (SEQ ID NO:5)
             Pro Lys Lys Asp Arg Ala Arg Gln
```

To introduce the mutations, the following mismatch oligonucleotides were used as primers:

```
Mutation 1: Mut_Ala:
GA CCA AAG AAA GAT GCC GCA AGA CAA G  (SEQ ID NO:6)
   Pro Lys Lys Asp Ala Ala Arg Gln   (SEQ ID NO:7)

Mutation 2: Mut_Gln:
GA CCA AAG AAA GAT CAG GCA AGA CAA G  (SEQ ID NO:8)
   Pro Lys Lys Asp Gln Ala Arg Gln   (SEQ ID NO:9)

Mutation 3: Mut_Pro:
GA CCA AAG AAA GAT AGG CCA AGA CAA G  (SEQ ID NO:10)
   Pro Lys Lys Asp Arg Pro Arg Gln   (SEQ ID NO:11)

Mutation 4: Mut_Lys-Pro:
GA CCA AAG AAA GAT AAG CCA AGA CAA G  (SEQ ID NO:12)
   Pro Lys Lys Asp Lys Pro Arg Gln   (SEQ ID NO:13)
```

The mutagenesis primers used are each detailed with the modified amino acid sequences obtained therewith. The regions with the bases or amino acids which are changed from the wild-type sequence are in italics.

In mutation 1, arginine$_{110}$ was replaced by a nonpolar alanine. In mutation 2, a polar, uncharged glutamine was introduced at the same position. In mutant 3, the alanine at position 111, not the basic arginine$_{110}$, was replaced by a proline. In mutant 4, two amino acids were replaced. In this case, lysine and proline were introduced in place of arginine$_{110}$ and alanine$_{111}$. After the mutagenesis had been carried out, the mutations were verified by sequence analysis. The resulting VEGF mutants had the following sequences for amino acids 109-112:

```
VEGF_165 wild type:  -Asp_109 Arg_110 Ala_111 Arg_112- (SEQ ID NO:14)

Mut_Gln:             -Asp_109 Gln_110 Ala_111 Arg_112- (SEQ ID NO:15)

Mut_Ala:             -Asp_109 Ala_110 Ala_111 Arg_112- (SEQ ID NO:16)

Mut_Pro:             -Asp_109 Arg_110 Pro_111 Arg_112- (SEQ ID NO:17)

Mut_Lys-Pro:         -Asp_109 Lys_110 Pro_111 Arg_112- (SEQ ID NO:18)
```

The mutants Mut$_{Pro}$ and Mut$_{Lys-Pro}$ are mutants according to the invention, whereas Mut$_{Gln}$ and Mut$_{Ala}$ are produced and investigated for the purposes of comparison. The resulting VEGF$_{165}$ expression vectors were used in the further investigations.

Production of Recombinant VEGF$_{165}$ Protein

VEGF$_{165}$ protein was expressed in eukaryotic COS-1 cells. The pcDNA 3.1 expression vector used comprises an SV-40 origin of replication. This serves to amplify the vector in cells which express a large T antigen of the SV-40 virus. The COS-1 cells used possess a corresponding element integrated into the genome, so that episomal replication of the vector results. Expression of the target protein VEGF for several days is achieved thereby without stable integration (transformation) of the vector into the cell genome. The COS-1 cells were transfected with the expression plasmids obtained in the mutagenesis. For this purpose, the Superfect transfection reagent (QIAGEN, Hilden) was used according to the manufacturer's protocols.

Like a large number of growth factors, VEGF$_{165}$ also has a heparin-binding site which is located at the basic C terminus. The binding to heparin was exploited for purification of the protein by affinity chromatography (Mohanraj et al. 1995). The VEGF and VEGF variants were isolated by the following steps:

The COS-1 cells transformed with the expression plasmids were cultivated in serum-free DMEM (Dulbecco's modified Eagle's medium) comprising 10% fetal calf serum (FSC), 2 mM L-glutamine, penicillin (10 U/ml) and streptomycin (10 μg/ml) and ITS supplement (Sigma, Deisenhofen). Conditioned medium (200 ml) was collected after 48 h and incubated with 5 ml of heparin-Sepharose (Pharmacia, Freiburg) at 4° C. for 4 hours. The heparin-Sepharose was packed into a column. The latter was loaded with culture medium at a flow rate of 25 ml/h. The following steps were carried out:

A: Affinity chromatography with heparin-Sepharose
  1. Washing: 0.1 M NaCl; 20 mM Tris/pH 7.2
  2. Washing: 0.3 M NaCl; 20 mM Tris/pH 7.2
  3. Elution: 0.9 M NaCl; 20 mM Tris/pH 7.2

B: Analysis of the resulting fractions by Western blot analysis

C: Desalting of the VEGF-containing fractions by gel filtration

Running buffer: 10 mM Tris/pH 7.2

D: Lyophilization of the solution and determination of the concentration by ELISA The resulting VEGF was investigated by SDS-PAGE. The VEGF protein obtained from COS-1 cells differs in its migration behaviour in SDS-PAGE from the commercially available VEGF$_{165}$ protein used (from R&D Systems). In addition to the signal to be detected at 42 kDA (FIG. 1, lane 6), a further band with a molecular weight which is a few kDA higher is also evident. The reason for this double band of the VGEF protein expressed in COS-1 cells is an altered glycosylation of the growth factor. On expression of VEGF in COS-1 cells there is formation of two differently glycosylated proteins. One form (42 kDa) is identical in its glycosylation to the recombinant VEGF$_{165}$ which has been used to date and which was produced in insect cells using a baculovirus expression system (R&D Systems, FIG. 1, lane 1). It has an N-glycosylation on the amino acid asparagine at position 74 (Gospodarowicz et al. 1989; Keck et al. 1989). The second band at a higher molecular weight (45 kDa) results from further glycosylation of the protein. The difference in the glycosylation is known for expression in COS cells and has no effect on the biological activity of the growth factor (R&D Systems).

Characterization of the Biochemical and Biological Properties of the Purified VEGF$_{165}$ Proteins I. Analysis of the Stability of the VEGF$_{165}$ Proteins and its Mutations:

a) Incubation in Plasmin

The four purified mutated VEGF proteins were initially investigated for their stability towards the protease plasmin. It was investigated whether the mutations carried out lead to an altered degradation behaviour compared with wild-type VEGF.

FIG. 1 shows the results of incubation of the VEGF wild type and the VEGF mutants with plasmin. Incubation of the VEGF wild type synthesized in COS-1 cells (A, lane 6-10) shows degradation of the growth factor after only 15 minutes. In this case, accurate determination of the size of the resulting fragments by SDS-PAGE is difficult because the signals overlap with the two bands of the differently glycosylated protein. However, the degradation pattern is similar to that of the commercially obtainable VEGF$_{165}$ (FIG. 1A, lane 1-5). Thus, a fragment with a molecular weight of 38 kDA can be detected after 45 minutes. This corresponds to the 110 dimer fragment of the less glycosylated VEGF variant. These results clearly show that the VEGF protein expressed in the COS-1 cells is also cleaved by plasmin under the chosen conditions.

FIG. 1B (lane 1-17) shows the results of incubation of mutated proteins. Incubation of the arginine to alanine mutation is shown first (lane 1-5). At zero incubation time, two bands are detectable for the differently glycosylated variants of the VEGF protein, as with the wild type. However, in this case, because of the higher signal intensity, they cannot be differentiated from one another so clearly as with the VEGF$_{165}$ wild type. In contrast to the VEGF wild type, the mutated protein shows no change in the migration behaviour up to 240 minutes after incubation.

This observation suggests that the arginine$_{110}$ to alanine$_{110}$ mutation has led to inactivation of the plasmin cleavage site. As shown further in FIG. 1B, the three other mutants Mut$_{Pro}$, Mut$_{Gln}$ and Mut$_{Lys-Pro}$ also show a comparable stability of the signal bands at 45 and 42 kDA after incubation with plasmid for 240 minutes. A control in which the VEGF$_{165}$ wild type was incubated with plasmin buffer at 37° C. for 4 hours is not degraded (lanes 18 and 19). Overall, these experiments indicate that the produced and purified VEGF mutants are stable towards the protease plasmin.

b) Incubation in Acute and Chronic Wound Fluid

In the next step, the degradation of the VEGF mutants in wound fluid from patients with acute and chronic wounds was analysed. On incubation of the VEGF$_{165}$ wild type and all VEGF mutants in acute wound fluid, no degradation was detectable after 240 minutes.

Figure 2:
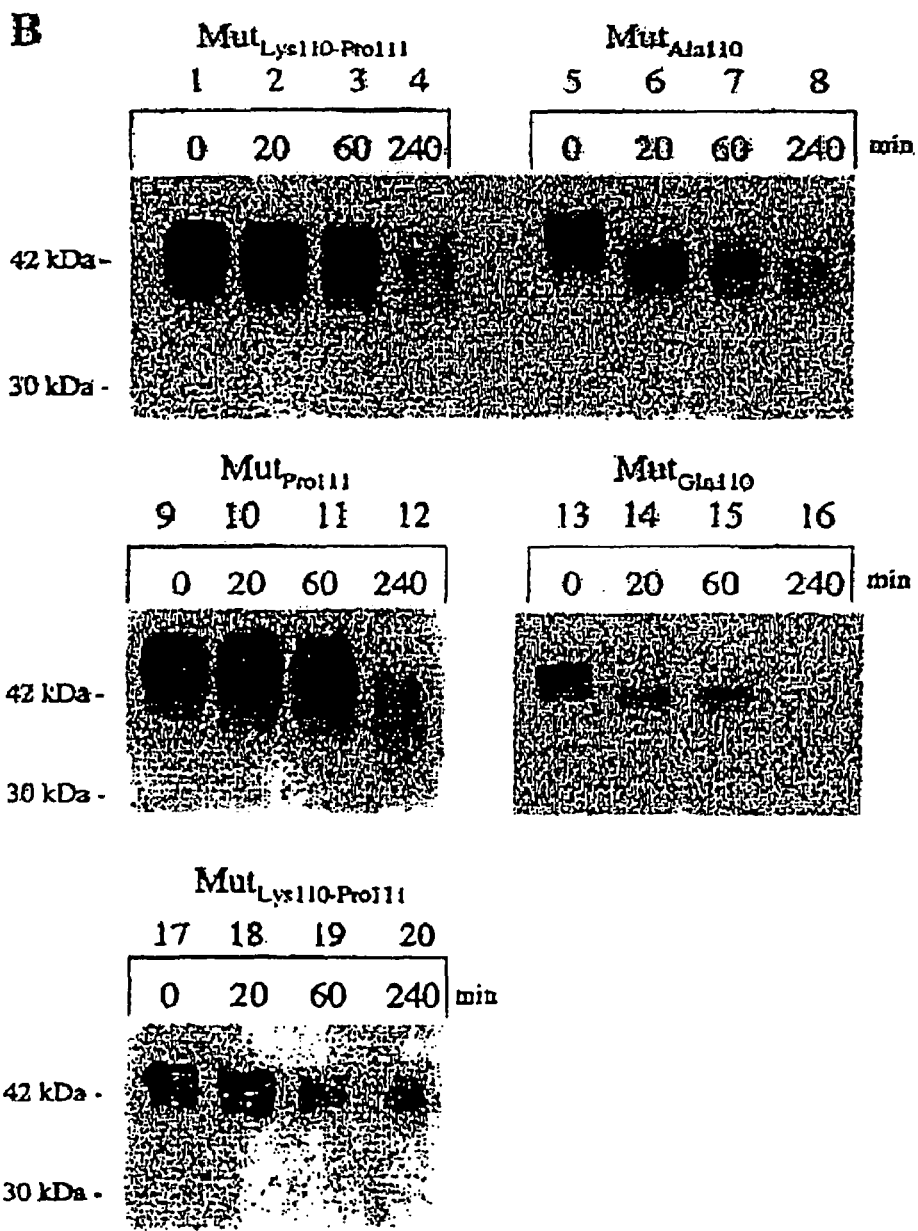
Figure 2:
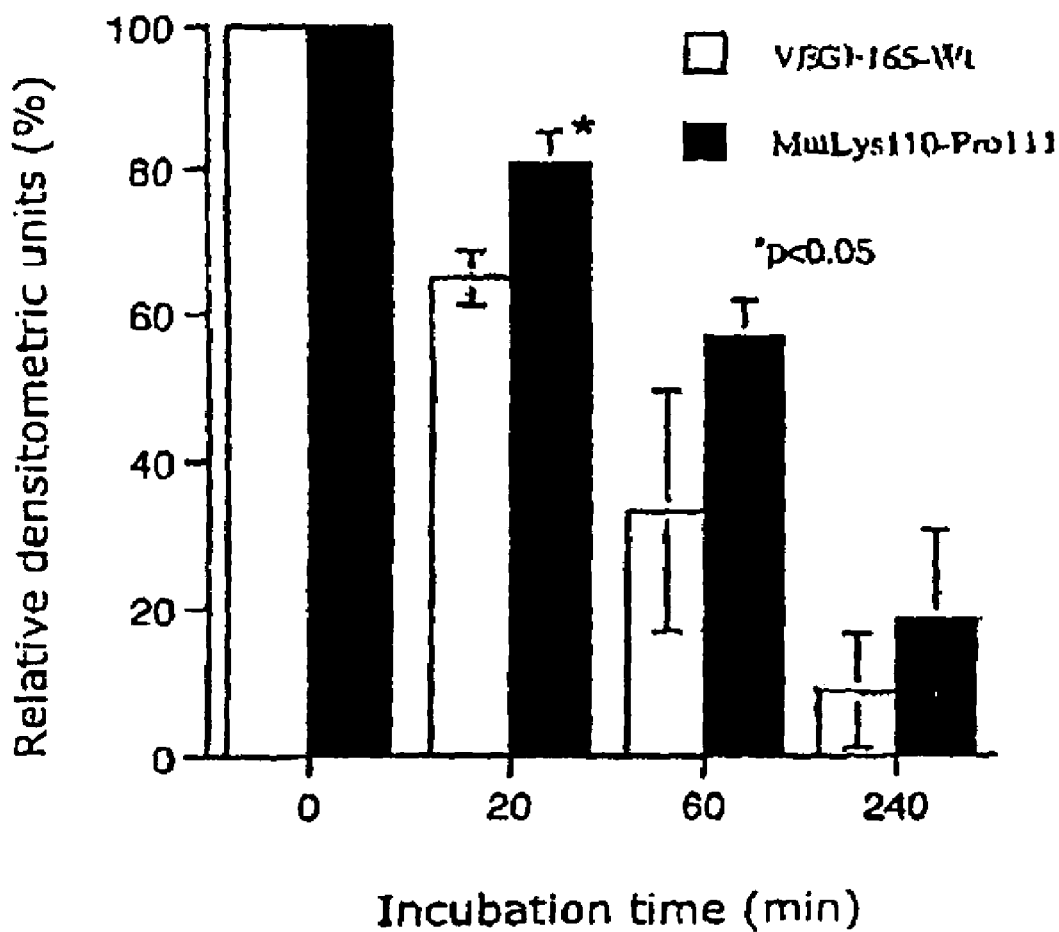

FIG. 2 shows the effect of chronic wound fluid on the stability of the VEGF proteins. Incubation of the VEGF wild type synthesized in COS-1 cells (FIG. 2A, lane 1-4) for 240 minutes shows degradation of the growth factor with a fragment of about 38 kDa. This corresponds to the 110 dimer fragment of the less glycosylated VEGF variant.

In contrast to the wild type, the VEGF$_{65}$ mutants show a different degradation behaviour on incubation in chronic wound fluid. On the one hand, the degradation process observed in the mutations Mut$_{Gln}$ (FIG. 2B, lanes 13-16 and Mut$_{Ala}$ (lanes 5-8) is comparable to that of the wild type. Fragments with a molecular weight of about 38 kDa are produced after only about 20 min.

On the other hand, analysis of the mutants Mut$_{Pro}$ (lanes 9-12) and Mut$_{Lys-Pro}$ (Lanes 1-4, 17-20) shows a breakdown behaviour different from the wild type and the mutants Mut$_{Ala}$ and Mut$_{Gln}$. A stable signal at 42 and 45 kDa is seen in the SDS-PAGE up to 60 minutes after incubation. This indicates stabilization of the mutated proteins Mut$_{Pro}$ and Mut$_{Lys-Pro}$ in the chronic wound fluid. This difference in the degradation behaviour of the mutants with neutral/nonpolar amino acid and those with proline suggests that further proteases, besides plasmin, are involved in the breakdown of VEGF in the chronic wound environment.

Degradation is observable with all mutated proteins 240 minutes after incubation in chronic wound fluid. In these cases there is not just formation of clearly defined breakdown fragments; on the contrary, a diffuse signal between 38 and 45 kDa appears after 240 min. This presumably involves proteolysis in the region of the first 20 amino acids (recognition site of the antibody), because the signal strength decreases markedly after 240 min.

In summary, the results indicate that the VEGF mutants with proline at position 111 are initially stabilized in chronic wound fluid but are degraded in the long term. Comparable results were observed in the would fluids from three different patients with chronic venous insufficiency. The experiments for the various wound fluids were repeated at least twice (FIG. 2B: patient X lanes 1-4; patient Y lanes 17-20). The resulting band pattern always remained the same moreover.

FIG. 2C shows a densitometric evaluation of the breakdown of VEGF wild type and Mut$_{Lys-Pro}$. The aim of the investigation was to quantify the stabilization of the VEGF mutant in the chronic wound fluid. For this purpose, the time-dependent change in the signal strength at the level of the initial signal (42-45 kDa region) compared with the signal at time zero was determined. The densitometric densities measured at the various times are depicted as percentage of the initial signal. It is clear in this densitometric investigation that at every measurement time the VEGF mutant shows a stronger signal by comparison with the VEGF wild type in the 42-45 kDa region, and thus intact VEGF$_{165}$ protein is present. This observation suggests that this mutation leads to an improved stability and bioactivity of the VEGF protein in the chronic wound environment. The difference between wild type and mutant is statistically significant only 20 minutes after the incubation. The measurements were carried out with identical wound fluid for three independent experiments.

II. Investigations of the Biological Activity of VEGF$_{165}$ Wild Type and the Mutated Variants:

It was investigated whether the mutations have an effect on the biological activity of the VEGF molecule. The biological activity was assayed by means of a BrdU proliferation assay (Roche Diagnostics, Mannheim) on human umbilical vein endothelial cells (HUVE cells) in accordance with the manufacturer's information. This entailed the HUVE cells being cultivated with addition of various VEGF mutants, then incubated with BrdU solution for 6 hours and fixed, after which an ELISA was carried out using a BrdU-specific antibody.

Figure 3:
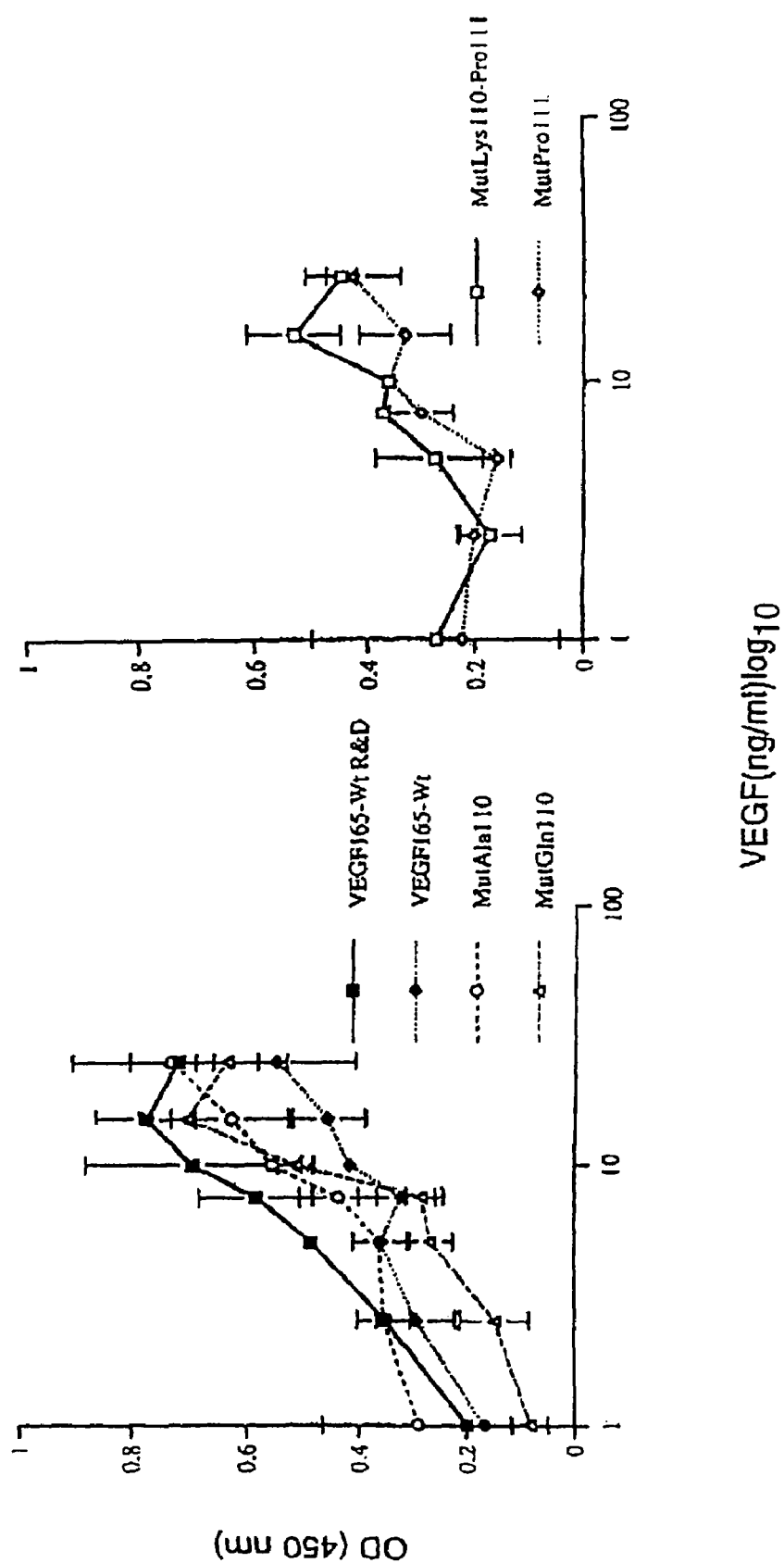

VEGF concentrations between 1 ng/ml and 25 ng/ml were employed. Commercially available recombinant VEGF$_{165}$ protein (R&D Systems) and VEGF$_{165}$ wild type synthesized in COS-1 cells showed a half-maximum stimulation of BrdU incorporation at about 3 ng/ml (FIG. 3). The mutated VEGF proteins are characterized by a stimulation of endothelial cell proliferation which is comparable to the VEGF wild type synthesized in COS-1 cells. The maximum stimulation of all the proteins synthesized in COS-1 cells was less than that by commercially obtainable VEGF$_{165}$ wild type. The reason for the difference between the two curved profiles may be the different expression systems and purification methods for the proteins (Mohanraj et al. 1995). The biological activity of VEGF$_{165}$ is thus not significantly affected by the mutations carried out.

The question of the extent to which the biological activity of the VEGF$_{165}$ wild type and of the VEGF mutants is affected after plasmin incubation was subsequently examined. For this purpose, the VEGF proteins were incubated with plasmin, and then the biological activity was investigated by means of a BrdU proliferation assay on HUVE cells.

Figure 4:
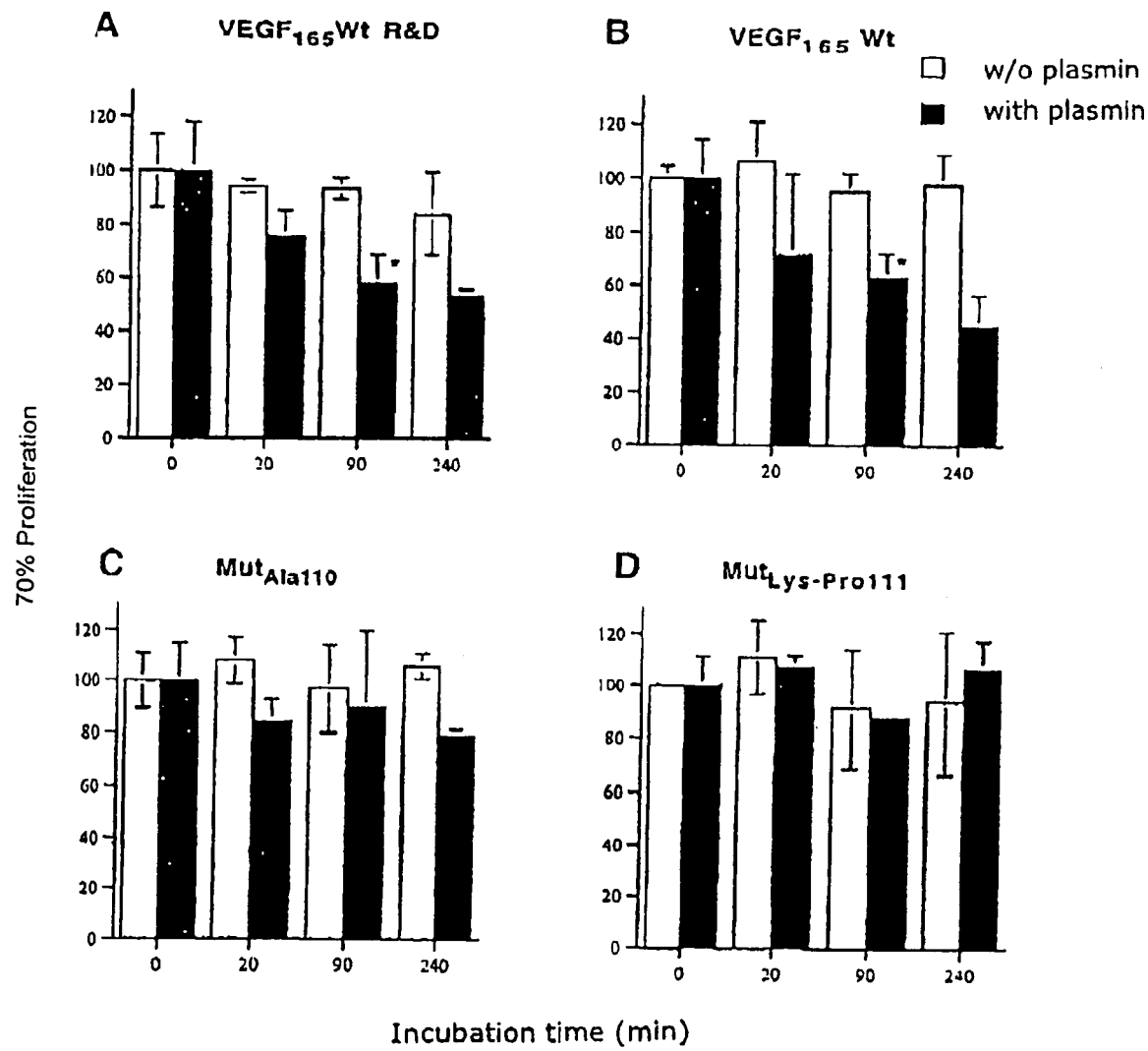

In the graphical representation (FIG. 4), the BrdU incorporation is shown as percentage of the initial signal (time t=0). Incubation of the VEGF wild types (synthesized in COS-1 cells and from R&D Systems) and of the VEGF mutants Mut$_{Ala}$ and Mut$_{Lys-Pro}$ in plasmin buffer at 37° C. shows no impairment of the biological activity of the proteins (FIG. 4A-D). In contrast thereto, incubation of the VEGF$_{165}$ wild types in plasmin leads to a marked reduction in the biological activity (FIG. 4A, B). An activity loss of at least 20% is seen only 20 minutes after incubation, and then falls further to about 50% of the initial activity after 240 minutes. The Mut$_{Ala}$ and Mut$_{Lys-Pro}$ mutants show no significant activity loss after incubation with plasmin (FIG. 4C, D). These results underline the "plasmin resistance" of the mutants demonstrated in the Western blot (FIG. 1) and show that the mutated proteins are stable even after incubation with plasmin.

The introduced mutations thus result in an inhibition of VEGF cleavage by plasmin. A stabilization of VEGF and thus an increased biological activity in the chronic wound environment can be brought about by the Ala$_{111}$ to Pro$_{111}$ mutation.

REFERENCES

Frank S, Hübner G. Breier G, et al., J Biol Chem 270:12607-12613, 1995.

Fukumura D, Xavier R, Sugiura T, et al., Cell 94:715-725, 1998.

Gospodarowicz D, Abraham J, Schilling J, Proc Natl Acad Sci 86:7311-7315, 1989.

Keck P, Hauser S, Krivi G, et al., Science 246:1309-1312, 1989.

Keyt B, Berleau L, Ngyen H, Chen H et al., J Biol Chem 271:7788-7795, 1996.

Lauer G, Sollberg S, Cole M, Flamme I, Stürzebecher J, Mann K, Krieg T, Eming S, J Invest Dermatol 115:12-18, 2000.

Lawrence W, Diegelann R, Clin Dermatol 12:157-169, 1994.

Mohanraj D, Olson T, Ramakrishnan S, et al., Growth Factors 12:17-27, 1995.

Nissen N, Polverini P, Koch A, et al., Am J Path 152:1445-1452, 1998.

Poers J, Odake S, Oleksyszyn J, Hori H et al., AAS 42:3-18, 1993.

Scharffetter-Kochanek, Meewes C, Eming S, et al., Z. Hautkrankheiten 74:239-249, 1999.

Soker S, Takashima S, Miao H, Neufeld G, Klagsbrun M et al., Cell 92:735-745, 1998.

Stryer T, in Biochemie. 4th edition 1987; Spektrum Akademischer Verlag.

---

What is claimed is:

1. A vascular endothelial growth factor (VEGF) variant, comprising an amino acid sequence, wherein said amino acid sequence is the amino acid sequence of a native vascular endothelial growth factor in which at least one amino acid at positions 110 or 111 of the native vascular endothelial growth factor is replaced by proline or is deleted.

2. The VEGF variant according to claim 1, wherein at least one further amino acid the other of the positions 110 or 111 is replaced or is deleted.

3. The VEGF variant according to claim 1, wherein an alanine at position 111 of the native vascular endothelial growth factor is replaced by proline.

4. The VEGF variant according to claim 3, wherein an arginine at position 110 of the native vascular endothelial growth factor is replaced by another amino acid.

5. The VEGF variant according to claim 4, wherein said another amino acid is proline.

6. The VEGF variant according to claim 1, wherein an arginine at position 110 of the native vascular endothelial growth factor is replaced by proline.

7. The VEGF variant according to claim 6, wherein an alanine at position 111 of the native vascular endothelial growth factor is replaced by another amino acid.

8. The VEGF variant according to claim 7, wherein said another amino acid is proline.

9. The VEGF variant according to claim 1, wherein the VEGF variant is in the form of any of the splice variants $VEGF_{121}$, $VEGF_{145}$, $VEGF_{165}$, $VEGF_{183}$, $VEGF_{189}$ or $VEGF_{206}$.

10. The $VEGF_{165}$ variant according to claim 9, wherein the $VEGF_{165}$ variant has one of the amino acid sequences

```
Seq. ID No. 1:
Ala Pro Met Ala Glu Gly Gly Gly Gln Asn His His
Glu Val Val Lys Phe Met Asp Val Tyr Gln Arg Ser
Tyr Cys His Pro Ile Glu Thr Leu Val Asp Ile Phe
Gln Glu Tyr Pro Asp Glu Ile Glu Tyr Ile Phe Lys
Pro Ser Cys Val Pro Leu Met Arg Cys Gly Gly Cys
Cys Asn Asp Glu Gly Leu Glu Cys Val Pro Thr Glu
Glu Ser Asn Ile Thr Met Gln Ile Met Arg Ile Lys
Pro His Gln Gly Gln His Ile Gly Glu Met Ser Phe
Leu Gln His Asn Lys Cys Glu Cys Arg Pro Lys Lys
Asp Arg Pro Arg Gln Glu Asn Pro Cys Gly Pro Cys
Ser Glu Arg Arg Lys His Leu Phe Val Gln Asp Pro
Gln Thr Cys Lys Cys Ser Cys Lys Asn Thr Asp Ser
Arg Cys Lys Ala Arg Gln Leu Glu Leu Asn Glu Arg
Thr Cys Arg Cys Asp Lys Pro Arg Arg
or
```

```
Seq. ID No. 2:
Ala Pro Met Ala Glu Gly Gly Gly Gln Asn His His
Glu Val Val Lys Phe Met Asp Val Tyr Gln Arg Ser
Tyr Cys His Pro Ile Glu Thr Leu Val Asp Ile Phe
Gln Glu Tyr Pro Asp Glu Ile Glu Tyr Ile Phe Lys
Pro Ser Cys Val Pro Leu Met Arg Cys Gly Gly Cys
Cys Asn Asp Glu Gly Leu Glu Cys Val Pro Thr Glu
Glu Ser Asn Ile Thr Met Gln Ile Met Arg Ile Lys
Pro His Gln Gly Gln His Ile Gly Glu Met Ser Phe
Leu Gln His Asn Lys Cys Glu Cys Arg Pro Lys Lys
Asp Lys Pro Arg Gln Glu Asn Pro Cys Gly Pro Cys
Ser Glu Arg Arg Lys His Leu Phe Val Gln Asp Pro
Gln Thr Cys Lys Cys Ser Cys Lys Asn Thr Asp Ser
Arg Cys Lys Ala Arg Gln Leu Glu Leu Asn Glu Arg
Thr Cys Arg Cys Asp Lys Pro Arg Arg.
```

11. The VEGF variant according to claim 1, wherein the amino acid chain is modified or derivatized and/or comprises mutations, insertions and/or deletions and/or has a signal sequence.

12. The VEGF variant according to claim 11, wherein the signal sequence is connected N-terminally to the amino acid chain of the VEGF variant and has the sequence of SEQ ID NO:3:

```
Met Asn Phe Leu Ser Trp Ser Val His Trp Ser Leu
Ala Leu Leu Leu Tyr Leu His His Ala Lys Trp Ser
Gln Ala.
```

13. A nucleic acid encoding the VEGF variant of claim 1.

14. Vectors comprising nucleic acids according to claim 13 for expression of said VEGF variant.

15. A medicament comprising VEGF variants according to claim 1.

16. A method for treating chronic wounds comprising administering to a patient in need thereof an effective amount of the VEGF variant of claim 1.

17. The VEGF variant according to claim 1, wherein the an amino acid at position 111 of the native vascular endothelial growth factor is replaced by proline or is deleted and wherein an amino acid at position 110 is maintained or replaced with lysine.

18. The VEGF variant according to claim 17, wherein the amino acid at position 111 of the native vascular endothelial growth factor is replaced by proline.

19. The VEGF variant according to claim 17, wherein the amino acid at position 110 of the native vascular endothelial growth factor is replaced by lysine.

* * * * *

UNITED STATES PATENT AND TRADEMARK OFFICE
CERTIFICATE OF CORRECTION

PATENT NO. : 7,491,696 B2  Page 1 of 1
APPLICATION NO. : 10/506893
DATED : February 17, 2009
INVENTOR(S) : Eming et al.

It is certified that error appears in the above-identified patent and that said Letters Patent is hereby corrected as shown below:

In column 3, please correct the paragraph starting on line 26 as follows:

-- The VEGF variants according to the invention may also have a signal sequence. The signal sequence may be connected N-terminally to the amino acid chain of the VEGF variant and have the sequence
(SEQ ID NO:3)
Met Asn Phe Leu Leu Ser Trp ~~Ser~~ Val His Trp Ser Leu Ala Leu
Leu Leu Tyr Leu His His Ala Lys Trp Ser Gln Ala --

In column 18, please correct the paragraph starting on line 34 (Claim 12) as follows:

-- 12. The VEGF variant according to claim 11, wherein the signal sequence is connected N-terminally to the amino acid chain of the VEGF variant and has the sequence of SEQ ID NO: 3:

Met Asn Phe Leu Leu Ser Trp ~~Ser~~ Val His Trp Ser Leu Ala Leu
Leu Leu Tyr Leu His His Ala Lys Trp Ser Gln Ala --

Signed and Sealed this

Twenty-eighth Day of September, 2010

David J. Kappos
*Director of the United States Patent and Trademark Office*

SEQUENCE LISTING

<160> NUMBER OF SEQ ID NOS: 18

<210> SEQ ID NO 1
<211> LENGTH: 165
<212> TYPE: PRT
<213> ORGANISM: Artificial
<220> FEATURE:
<223> OTHER INFORMATION: mutated human VEGF

<400> SEQUENCE: 1

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Pro Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
```

```
                130                 135                 140
Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 2
<211> LENGTH: 165
<212> TYPE: PRT
<213> ORGANISM: Artificial
<220> FEATURE:
<223> OTHER INFORMATION: mutated human VEGF

<400> SEQUENCE: 2

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Lys Pro Arg
                100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
        130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 3
<211> LENGTH: 26
<212> TYPE: PRT
<213> ORGANISM: Homo sapiens

<400> SEQUENCE: 3

Met Asn Phe Leu Ser Trp Ser Val His Trp Ser Leu Ala Leu Leu Leu
1               5                   10                  15

Tyr Leu His His Ala Lys Trp Ser Gln Ala
                20                  25

<210> SEQ ID NO 4
<211> LENGTH: 27
<212> TYPE: DNA
<213> ORGANISM: Homo sapiens

<400> SEQUENCE: 4
gaccaaagaa agatagagca agacaag                                       27

<210> SEQ ID NO 5
<211> LENGTH: 8
<212> TYPE: PRT
```

<213> ORGANISM: Homo sapiens

<400> SEQUENCE: 5

Pro Lys Lys Asp Arg Ala Arg Gln
1               5

<210> SEQ ID NO 6
<211> LENGTH: 27
<212> TYPE: DNA
<213> ORGANISM: Artificial
<220> FEATURE:
<223> OTHER INFORMATION: mutated human VEGF sequence

<400> SEQUENCE: 6
gaccaaagaa agatgccgca agacaag                                27

<210> SEQ ID NO 7
<211> LENGTH: 8
<212> TYPE: PRT
<213> ORGANISM: Artificial
<220> FEATURE:
<223> OTHER INFORMATION: mutated human VEGF fragment

<400> SEQUENCE: 7

Pro Lys Lys Asp Ala Ala Arg Gln
1               5

<210> SEQ ID NO 8
<211> LENGTH: 27
<212> TYPE: DNA
<213> ORGANISM: Artificial
<220> FEATURE:
<223> OTHER INFORMATION: mutated human VEGF sequence

<400> SEQUENCE: 8
gaccaaagaa agatcaggca agacaag                                27

<210> SEQ ID NO 9
<211> LENGTH: 8
<212> TYPE: PRT
<213> ORGANISM: Artificial
<220> FEATURE:
<223> OTHER INFORMATION: mutated human VEGF fragment

<400> SEQUENCE: 9

Pro Lys Lys Asp Gln Ala Arg Gln
1               5

<210> SEQ ID NO 10
<211> LENGTH: 27
<212> TYPE: DNA
<213> ORGANISM: Artificial
<220> FEATURE:
<223> OTHER INFORMATION: mutated human VEGF sequence

<400> SEQUENCE: 10
gaccaaagaa agataggcca agacaag                                27

<210> SEQ ID NO 11
<211> LENGTH: 8
<212> TYPE: PRT
<213> ORGANISM: Artificial
<220> FEATURE:
<223> OTHER INFORMATION: mutated human VEGF fragment

<400> SEQUENCE: 11

Pro Lys Lys Asp Arg Pro Arg Gln
1               5

<210> SEQ ID NO 12
<211> LENGTH: 27
<212> TYPE: DNA
<213> ORGANISM: Artificial
<220> FEATURE:
<223> OTHER INFORMATION: mutated human VEGF sequence

<400> SEQUENCE: 12
gaccaaagaa agataagcca agacaag                                          27

<210> SEQ ID NO 13
<211> LENGTH: 8
<212> TYPE: PRT
<213> ORGANISM: Artificial
<220> FEATURE:
<223> OTHER INFORMATION: mutated human VEGF fragment

<400> SEQUENCE: 13

Pro Lys Lys Asp Lys Pro Arg Gln
1               5

<210> SEQ ID NO 14
<211> LENGTH: 4
<212> TYPE: PRT
<213> ORGANISM: Homo sapiens

<400> SEQUENCE: 14

Asp Arg Ala Arg
1

<210> SEQ ID NO 15
<211> LENGTH: 4
<212> TYPE: PRT
<213> ORGANISM: Artificial
<220> FEATURE:
<223> OTHER INFORMATION: mutated human VEGF fragment

<400> SEQUENCE: 15

Asp Gln Ala Arg
1

<210> SEQ ID NO 16
<211> LENGTH: 4
<212> TYPE: PRT
<213> ORGANISM: Artificial
<220> FEATURE:
<223> OTHER INFORMATION: mutated human VEGF fragment

<400> SEQUENCE: 16

Asp Ala Ala Arg
1

<210> SEQ ID NO 17
<211> LENGTH: 4
<212> TYPE: PRT
<213> ORGANISM: Artificial
<220> FEATURE:
<223> OTHER INFORMATION: mutated human VEGF fragment

<400> SEQUENCE: 17

Asp Arg Pro Arg
1

-continued

```
<210> SEQ ID NO 18
<211> LENGTH: 4
<212> TYPE: PRT
<213> ORGANISM: Artificial
<220> FEATURE:
<223> OTHER INFORMATION: mutated human VEGF fragment

<400> SEQUENCE: 18

Asp Lys Pro Arg
1
```